United States Patent [19]
Mitchell et al.

[11] Patent Number: 5,388,351
[45] Date of Patent: Feb. 14, 1995

[54] CUBOID-NAVICULA NAVICULAR SUPPORT

[76] Inventors: Jane Mitchell; Thomas Pekar, both of 51 Mountain Street, St. Catharines, Ontario, L2T 2S6, Canada

[21] Appl. No.: 26,069

[22] Filed: Mar. 4, 1993

[51] Int. Cl.6 ............................................. A43B 7/22
[52] U.S. Cl. ........................................ 36/145; 36/91; 36/166
[58] Field of Search ................ 36/88, 91, 71, 145, 36/166, 180

[56] References Cited

U.S. PATENT DOCUMENTS

| | | | |
|---|---|---|---|
| 1,578,715 | 3/1926 | Cooke | 36/145 |
| 1,957,695 | 5/1934 | Chiappetta . | |
| 1,986,646 | 1/1935 | Schade | 36/177 |
| 1,997,504 | 4/1935 | Wisbrun | 36/180 |
| 2,036,890 | 4/1936 | Slater | 36/180 |
| 2,088,707 | 8/1937 | King . | |
| 2,089,384 | 8/1937 | Levitt | 36/145 |
| 2,154,997 | 4/1939 | Schipper | 36/166 |
| 2,238,366 | 4/1941 | Leydecker | 36/180 |
| 2,589,163 | 3/1952 | Tieman | 36/180 |
| 3,265,071 | 8/1966 | Kirchner et al. | 36/145 |
| 4,316,334 | 2/1982 | Hunt | 36/91 |
| 4,442,612 | 4/1984 | Hauser | 36/91 |
| 4,627,177 | 12/1986 | Meyers | 36/91 |
| 4,686,994 | 8/1987 | Harr et al. . | |
| 5,129,395 | 7/1992 | Hoffmann | 36/166 |
| 5,164,878 | 11/1992 | Hauser | 36/166 |

FOREIGN PATENT DOCUMENTS

| | | | |
|---|---|---|---|
| 4865 | of 1895 | United Kingdom | 36/166 |
| 2111821 | 7/1983 | United Kingdom | 36/91 |

*Primary Examiner*—Paul T. Sewell
*Assistant Examiner*—Marie Denise Patterson
*Attorney, Agent, or Firm*—Lowe, Price, LeBlanc & Becker

[57] ABSTRACT

An arch support is provided for treatment of problems arising from the displacement of the cuboid-navicular arch, the support comprising a base portion having a rear edge and a front edge, a top portion raised above the base, a first surface sloping upwardly and forwardly from the base rear edge to the top portion, and a second surface sloping downwardly and forwardly from the top portion to the base front edge, wherein the maximum depth of the arch support is in the region of the top portion adjacent the first surface for engaging the cuboid-navicular arch of the foot.

15 Claims, 2 Drawing Sheets

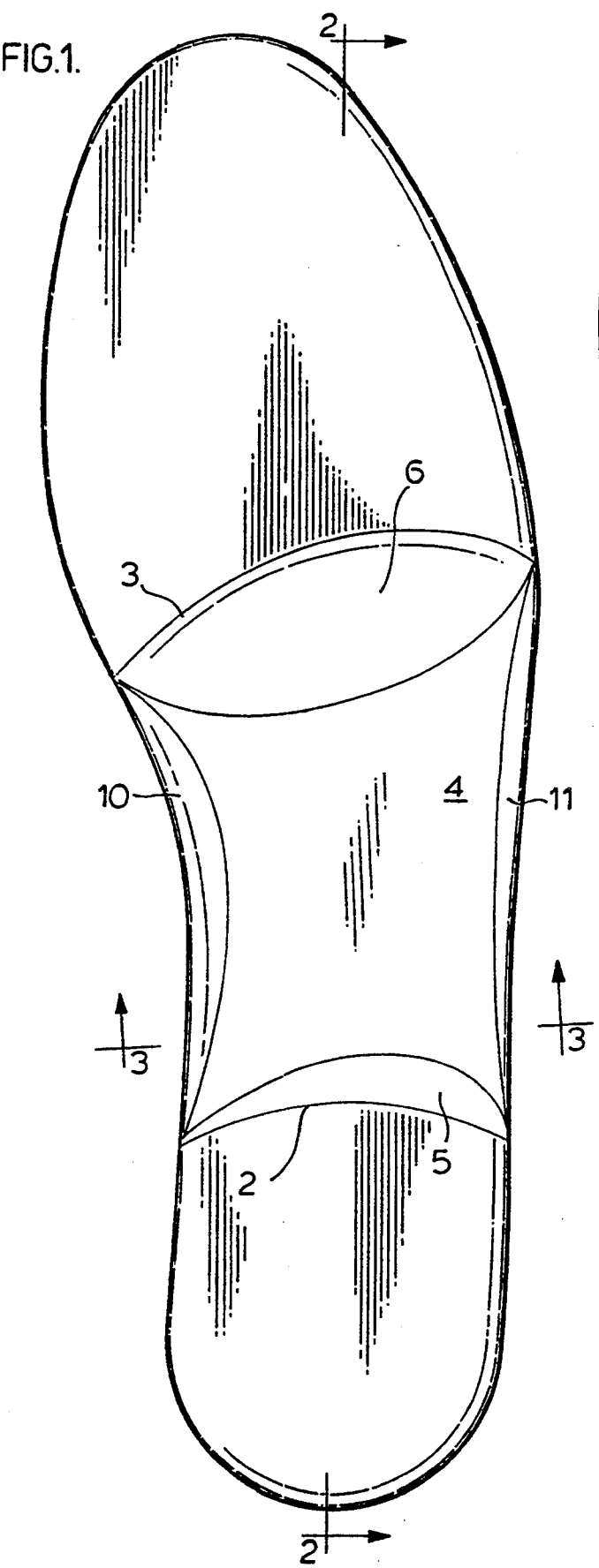
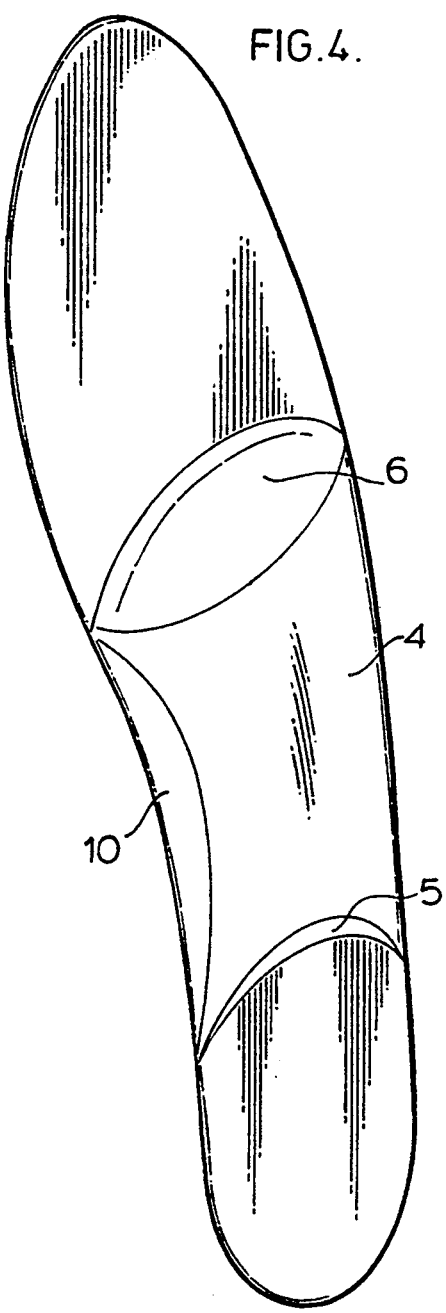

CUBOID-NAVICULA NAVICULAR SUPPORT

This invention relates to remedial orthotic devices and more particularly to an orthotic device which provides correction for problems of the cuboid-navicular arch and midfoot arch.

BACKGROUND OF THE INVENTION

A variety of orthotic devices are available which provide support to the medial longitudinal arch of the foot, as seen for example in U.S. Pat. Nos. 3,265,071; 4,686,994; and 5,164,878. These devices act to prevent further subluxation of the bones of the feet but at the same time, however, they prevent correction of any misalignment of the cuboid navicular and midfoot arches by holding the position of the navicula and medial longitudinal arch in a superior aspect. If the navicular is held in a superior aspect, the cuboid cannot rotate superiorly and laterally. The cuboid navicular arch and midfoot arch are then in subluxed position.

The device of U.S. Pat. No. 5,129,394 to Hoffmann uses an inclined plans inserted under the calcaneus bone but provides a gap between the central portion of the device and the midfoot. This device therefore leaves the foot unsupported in the area of the midfoot and the cuboid navicular arch.

While this device addresses the stabilization of pronation of gait, it does not address misalignment of the cuboid-navicula arch or the midfoot arch.

None of the previously available orthotic devices provide corrective support for the cuboid navicular arch.

SUMMARY OF THE INVENTION

The orthotic device of the invention engages the cuboid navicular arch of the foot, providing support and correcting any misalignment of the bones due to collapse of this arch.

In accordance with one embodiment of the invention, an arch support device is provided for treatment of problems arising from displacement of the cuboid-navicula arch of the foot, and comprises a base portion having a rear arch of the foot, and comprises a base surface having a predetermined length extending from a rear edge to a front edge;

a top surface raised above the base surface and having a predetermined length and a region of maximum height relative to the base surface;

a rear surface sloping upwardly and forwardly from the rear edge of the base surface to the top surface; and a front surface sloping downwardly and forwardly from the top surface to the front edge of the base surface, wherein the region of maximum height of the top surface relative to the base surface is located adjacent to the rear surface and is located during use underneath the cuboid-navicular arch of the foot for engaging the cuboid-navicular arch in supporting the foot, whereby a medial edge of the cuboid bone is lifted and a medial edge of the navicular bone is allowed to rotate downwardly.

BRIEF DESCRIPTION OF THE DRAWINGS

Certain embodiments of the invention are described, reference being made to the accompanying drawings wherein:

FIG. 1 is a top view of an arch support for a right foot in accordance with the invention, the support being shown as part of an insole.

FIG. 4 is a perspective view of a support in accordance with the invention, shown as part of an insole.

DETAILED DESCRIPTION OF THE INVENTION

Figure 2:
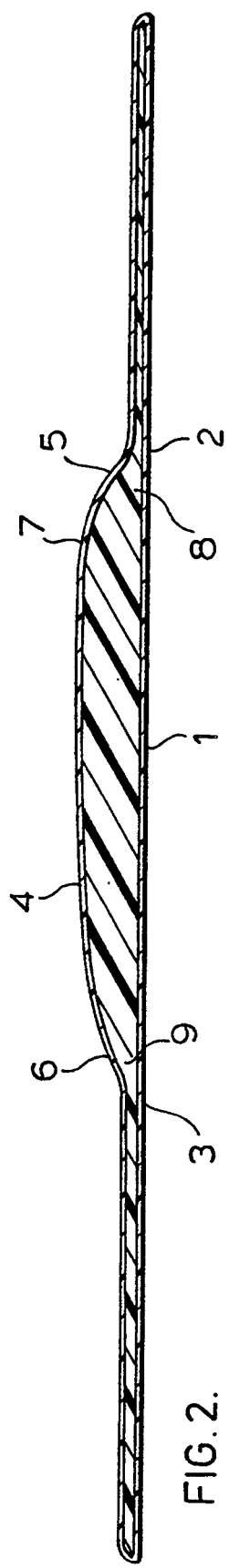
FIG. 2 is a cross-section along line 2—2 of FIG. 1.
Figure 3:
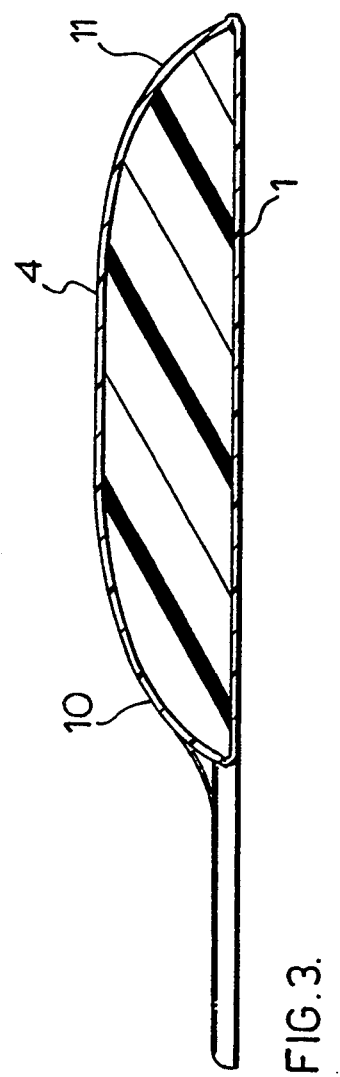
FIG. 3 is a cross-section along line 3—3 of FIG. 1.

FIGS. 1 to 4 illustrate a preferred embodiment of the arch support of the invention.

With reference to FIGS. 1 to 4, the support comprises a base 1 having a rear edge 2 and a front edge 3. A top portion 4 is raised above the base and engages the cuboid navicular and midfoot arches.

A first surface 5 slopes upwardly and forwardly from the rear edge 2 which has a concave arcuate shape (as best seen in FIG. 1) to the top portion 4 and a second surface 6 slopes downwardly and forwardly from the top portion 4 to the front edge 3.

The highest part of the surface of top portion 4 relative to the base 1 is a region 7 adjacent the first surface 5. This region of the support lies underneath and engages the cuboid-navicular arch of the foot. The first surface 5 preferably slopes upwardly from the base at an angle 8 of about 30° to about 46°. An angle of about 40° to about 45° is especially preferred.

The top portion 4 slopes forwardly and slightly downwardly from region 7. In accordance with the preferred embodiment, the top portion 4 extends forward to engage the cuneiform bones and proximal two-thirds of the metatarsal bones and blends into a convex second surface 6 which is curved transversely, causing front edge 3 to be convexly curved as seen in FIG. 1 and engages the transverse metatarsal arch of the foot at the metatarsal heads.

The top portion 4 may optionally terminate as far back as the metatarsal bases being sloped into a second surface which integrates the top portion to the base.

In accordance with the preferred embodiment, the height of region 7 relative to the base is preferably about 8% to about 14% of the length of the base 1, where the length is measured from front edge 3 to rear edge 2 along line 2—2, and the horizontal distance between region 7 where it engages the cuboid-navicular arch and the rear edge 2 of base 1 is about 10% to 20% of the length of base 1. A horizontal distance of about 15% to about 20% is especially preferred.

For average adult foot sizes, the height of region 7 relative to the base 1 may be about 0.3 inches to about 0.6 inches.

The top portion 4 may preferably slope downwardly from region 7 at an angle of about 2° to about 10° to the horizontal and the second surface 6 preferably forms an angle 9 of about 10° to about 16° with the base 1.

In accordance with the preferred embodiment, the length of top portion 4 from front to rear is preferably about 50% to about 60% of the length of base 1, a length of 55% to 60% being especially preferred.

As will be understood by those skilled in the art, where top portion 4 terminates further back, its length may be a smaller percentage of the length of the base.

A first side portion 10 slopes downwardly and medially from top portion 4 to base 1 forming a surface which engages the medial longitudinal arch of the foot. A second side portion 11 slopes downwardly and laterally from top portion 4 to base 1 forming a surface which engages the fifth metatarsal of the foot.

In accordance with a preferred embodiment, the horizontal extent of each side portion is approximately 10% of the width of the base 1 at line 3—3. Side portions 10 and 11 form an angle of about 30° to about 45° with the base and curve smoothly downwards from top portion 4.

As will be understood by those skilled in the art, an arch support in accordance with the invention may be made in various sizes to accommodate different foot sizes.

A common abnormality of the cuboid-navicular arch involves relative rotation of the cuboid and navicular bones so that the medial edge of the cuboid is displaced inferiorly and the medial edge of the navicular bones is displaced superiorly.

The arch support of the present invention engages the cuboid-navicular arch and pushes the medial edge of the cuboid bone upwardly while allowing the medial edge of the navicular bones to rotate downwardly. The device of the invention pushes the foot arches upward from the cuboid-navicular arch to the head of the metatarsals.

Use of the arch support of the invention, by supporting the cuboid and navicular bones in a more normal position, provides relief from foot pain resulting from misalignment of the cuboid-navicular arch, midfoot and metatarsal arches.

Additionally, this type of orthotic device is designed to assist in the restoration of foot arches by holding the bones in their proper relative position rather than supporting them in their collapsed position.

In some subjects, repositioning of the cuboid and navicular occurs, creating a more rounded cuboid-navicula arch.

The arch formed by the cuboid and navicular bones of the foot is moved superiorly. Proximal to the cuboid and navicular bones, the delineation is increased between the cuboid and calcaneus. This separation allows the calcaneus to move into a position which is parallel to the load-bearing surface. The talus, which sits on top of the calcaneus, also moves into a position which is parallel to the load-bearing surface. The repositioning of these bones allows the structures above them to realign. The fibula is permitted to rotate anteriorly and medially, and is able to be more useful in balance. Therefore overall balance is improved. Distal to the cuboid and navicular bones, the midfoot cuneiform bones and metatarsal bones are repositioned. The fourth and fifth metatarsals are shifted superiorly and laterally. The metatarsal arch is somewhat restored. This results in better push-off in gait.

The arch support of the invention may also be used in conjunction with a medial wedge placed under the medial aspect of the heel to stabilise the calcaneus for example when this bone is inverted or excessively exerted.

In accordance with a preferred embodiment of the invention, the arch support may be constructed as the central portion of an insole, as seen in FIG. 1. It may also be made as an independent central correction which may be fastened to existing footwear, for example by gluing or by means of adhesive tape.

In accordance with a further embodiment, the device may be incorporated into the sole of a shoe or other footwear during construction so as to form part of the shoe.

The arch support of the invention should be constructed from a material of sufficient density to maintain the foot arches in their desired positions throughout the gait cycle. Suitable materials include dense polyurethane foam, ethyl vinyl acetate, rubber, plastics or graphite sheeting. Polyurethane foam or graphite sheeting are preferred.

Leather or cotton materials may also be employed.

Polyurethane foam may be fashioned into arch supports by open-pour molding.

If desired for greater comfort, the device may optionally be covered on its top surface with softer materials, such as less dense polyurethane foam.

The present invention is not limited to the features of the embodiments described herein, but includes all variations and modifications within the scope of the claims.

We claim:

1. An arch support for treatment of problems arising from displacement of the cuboid-navicular arch formed by the cuboid bone and the navicular bone of a user's foot, comprising:
    a base surface having a predetermined length extending between a rear edge and a front edge;
    a top surface raised above the base surface and having a predetermined length and a region of maximum height relative to the base surface;
    a rear surface sloping upwardly and forwardly from the rear edge of the base surface to the top surface; and
    a front surface sloping downwardly and forwardly from the top surface to the front edge of the base surface,
    wherein the region of maximum height of the top surface relative to the base surface is located adjacent to the rear surface and is fit so that the maximum height is located during use just forwardly of the calcaneus and underneath the cuboid-navicular arch of the foot for engaging the cuboid-navicular arch in supporting the foot, whereby a medial edge of the cuboid bone is lifted and a medial edge of the navicular bone is allowed to rotate downwardly.

2. The arch support as in claim 1, wherein:
    the front surface is disposed to engage heads of metatarsals of the supported foot in use.

3. The arch support as in claim 1, wherein:
    a medial side portion of the top surface slopes downwardly and medially to the base and a lateral side portion of the top surface slopes downwardly and laterally to the base.

4. The arch support in accordance with claim 2, wherein:
    the height of the region of maximum height relative to the base is about 8% to about 14% of the length of the base.

5. The arch support in accordance with claim 1, wherein:
    the maximum height is about 0.3 inches to about 0.6 inches.

6. The arch support in accordance with claim 1, wherein:
    the rear surface slopes upwardly at a first angle of about 30° to about 46° with respect to the base.

7. The arch support in accordance with claim 6, wherein:
    the first angle is about 40° to about 45° with respect to the base.

8. The arch support in accordance with claim 1, wherein:

a distance between the base rear edge and the region of maximum height relative to the base surface is about 10% to about 20% of the length of the base surface.

9. The arch support in accordance with claim 8, wherein:
said distance is about 15% to about 20% of the length of the base surface.

10. The arch support in accordance with claim 1, wherein:
the front edge and the rear edge of the base surface are both arcuate in shape.

11. The arch support in accordance with claim 1, wherein:
the length of the top surface between the front and rear surfaces is about 50% to about 60% of the length of the base surface.

12. The arch support in accordance with claim 11, wherein:
the length of the top surface between the front and rear surfaces is about 55% to 60% of the length of the base surface.

13. The arch support in accordance with claim 1, wherein:
the top surface slopes forwardly and downwardly from the region of maximum height relative to the base at a second angle of about 2° to about 10° to the base surface.

14. The arch support in accordance with claim 13, wherein:
the top surface slopes forwardly and downwardly from the region of maximum height relative to the base at an angle of about 2° to the base surface.

15. The arch support in accordance with claim 1, wherein:
the support comprises one of polyurethane foam, ethyl vinyl acetate, rubber, plastics material, graphite sheeting, leather and cotton.

* * * * *